(12) United States Patent
Khanuja et al.

(10) Patent No.: US 6,858,588 B2
(45) Date of Patent: Feb. 22, 2005

(54) **NITRILE GLYCOSIDE USEFUL AS A BIOENHANCER OF DRUGS AND NUTRIENTS, PROCESS OF ITS ISOLATION FROM *MORINGA OLEIFERA***

(75) Inventors: Suman Preet Singh Khanuja, Lucknow (IN); Jai Shanker Arya, Lucknow (IN); Ranganathan Santha Kumar Tiruppadiripuliyur, Lucknow (IN); Dharmendra Saikia, Lucknow (IN); Harpreet Kaur, Lucknow (IN); Monika Singh, Lucknow (IN); Subhash Chandra Gupta, Lucknow (IN); Ajit Kumar Shasany, Lucknow (IN); Mahendra Pandurang Darokar, Lucknow (IN); Santosh Kumar Srivastava, Lucknow (IN); Madan Mohan Gupta, Lucknow (IN); Subash Chandra Verma, Lucknow (IN); Anirban Pal, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/403,814

(22) Filed: Mar. 31, 2003

(65) Prior Publication Data

US 2004/0198669 A1 Oct. 7, 2004

(51) Int. Cl.$^7$ .................. A61K 31/70; A61K 31/7028; C07H 15/00; C07C 255/32
(52) U.S. Cl. .................. 514/25; 514/519; 536/4.1; 558/303
(58) Field of Search .................. 514/25, 529, 4.1; 558/303

(56) References Cited

U.S. PATENT DOCUMENTS

2002/0151505 A1 * 10/2002 Fahey .................. 514/23

OTHER PUBLICATIONS

Guevara et al. (Mutation Research (1999), 440 (2), 181–188) (Abstract Sent).*
Leuck et al. (Carbohydrate Research (1998), 312 (1–2), 33–44). (Abstract Sent).*
A.P. Guevara et al.; "An Antitumor Promoter from Moringa Oleifera Lam"; Mutation Research, Amsterdam, NL, vol. 440, No. 2, 1999, pp. 181–188, XP001128727; ISSN: 0027–5107, p. 182.
U. Eilert et al.; "The Antibiotic Principle of Seeds of Moringa Oleifera and Moringa Stenopetala"; Planta Medica (1981), 42(1), 55–61, 1981 XP009024217 The Whole Document.
Akira Mukakami, et al.; "Niaziminin, A Thiocarbamate from The Leaves of Moringa Oleifera, Holds A Strick . . . Activation" Planta Medica (1998): 64(4), 319–323, 1998, XP009024218, The Whole Document.
Michael Leuck et al.; "Synthesis of Active Principles from the Leaves of Moringa Oleifera . . . Enylthiolgycosides" Carbohydrate Research (1998), 312(1–2), 33–44, 1998, XP004204817, The Whole Document.
Alemayehu Mekonen, et al.; "Chemical Investigation of the Leaves of Moringa Stenopetala" Bulletin of the Chemical Society of Ethiopia (2000), 14(1), 51–55, 2000, XP009024259, The Whole Document.

* cited by examiner

*Primary Examiner*—Elli Peselev
*Assistant Examiner*—Michael C. Henry
(74) *Attorney, Agent, or Firm*—Ladas & Parry (57) ABSTRACT

The present invention relates to a novel nitrile glycoside of Formula I named NIAZIRIDIN and to analogues and derivatives thereof. The present invention also relates to a process for the isolation of a novel nitrile glycoside of Formula I below named NIAZIRIDIN and its derivatives and analogues by bioactivity-guided fractionation from the pods of *Moringa oleifera*. The present invention particularly relates to the bioenhancing activity of the novel nitrile glycoside of Formula I below named NIAZIRIDIN and its derivatives and analogues in enhancing bioactivity of commonly used antibiotics such as rifampicin, tetracycline and ampicillin against Gram (+) and (−) bacteria. The biomolecule also enhances the absorption of drugs, vitamins and nutrients through the gastro-intestinal membrane increasing their bioavailability. Therefore niaziridin can be used in combination therapy with drugs and nutrients resulting in reduced drug associated toxicity, reduced cost and duration of chemotherapy.

Formula I

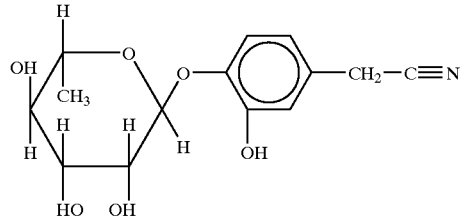

Niaziridin (1)

21 Claims, 2 Drawing Sheets

Figure 1

\* Comp.1 = Niaziridin @ 0.1 ug/ml.

* Rif = Rifampicin; B12 = Vitamin B-12; Comp.1 = Niaziridin.
Rif was monitored at 340 nm and Vit.B12 at 360 nm

US 6,858,588 B2

NITRILE GLYCOSIDE USEFUL AS A BIOENHANCER OF DRUGS AND NUTRIENTS, PROCESS OF ITS ISOLATION FROM *MORINGA OLEIFERA*

FIELD OF THE INVENTION

The present invention relates to a novel nitrile glycoside of Formula I named NIAZIRIDIN and to analogues and derivatives thereof. The present invention also relates to a process for the isolation of a novel nitrile glycoside of Formula I below named NIAZIRIDIN and its derivatives and analogues by bioactivity-guided fractionation from the pods of *Moringa oleifera*. The present invention particularly relates to the bioenhancing activity of the novel nitrile glycoside of Formula I below named NIAZIRIDIN and its derivatives and analogues in enhancing bioactivity of commonly used antibiotics such as rifampicin, tetracycline and ampicillin against Gram (+) and (−) bacteria. The biomolecule also enhances absorption of drugs, vitamins and nutrients through the gastro-intestinal membrane thereby increasing their bio-availability. Therefore niaziridin can be used in combination therapy with drugs and nutrients resulting in reduced drug associated toxicity, reduced cost and duration of chemotherapy.

Niaziridin (1)

Formula I

BACKGROUND OF THE INVENTION

Infectious diseases caused by bacteria and fungi affect millions of people worldwide, and in US alone cause a disease burden of more than $20 billion annually. Concerted and systemic programs to discover and develop new antibiotics and antifungals have been driven to a considerable extent by the development of resistance by these organisms to the drugs commonly used against them. However, due to the indiscriminate use of antibiotics resistance to even relatively new antibiotics such as vancomycin and methicillin are already reported in Enteroccocci and Staphylococci respectively. According to the Pharmaceutical Research and Manufacturers of America (PhRMA) there were 27 antibiotics and 12 antifungals under development in 1998 against bacterial and fungal infections in all stages of clinical development. At present, about 100 or so antibiotics are in the clinic. A key challenge to the antibiotic industry is that constant innovation is necessary not only because of resistance, but also because of side effects. Use of erythromycin a well-known macrolide antibiotic used as an alternative to patients, who are allergic to penicillins, exhibit strong gastrointestinal problems and also interact with the liver drug metabolizing enzymes. However, derivatives of erythromycin named azithromycin, dirithromycin are devoid of these problems. So, it is often possible to develop multiple analogs of successful antibiotics that achieve the same results with less adverse side effects. On the other hand these devices may increase the cost of chemotherapy. The clinical situation is much more complicated in cases where the chemotherapy has to be sustained for a longer duration (6–8 months) such as in antituberculosis therapy. The front-line antitubercular drugs rifampicin and isoniazid exhibit significant toxicity in mammalian systems. Gastric irritation, hepatitis, is some of the major side effects of nifampicin whereas, peripheral neuritis, anorexia, nausea, jaundice are associated with higher doses of isoniazid[22]. Under such situations to reduce the drug associated toxicity bioactivity enhancers (Bioenhancers) can be employed.

Bioenhancers are molecules, which do not possess drug activity of their own but promote and augment the biological activity or bioavailability or the uptake of drugs in combination therapy. Natural products especially from plant sources have played an important role in drug development of communicable diseases. Either the isolated plant biomolecules or its semi synthetic derivatives have provided useful clues in the production of medicines. According to WHO nearly 80% of the world's population relies on herbal medicines as primary health care. Synergism in which the action of one biomolecule is enhanced by another unrelated chemical has been the hallmark of herbal drugs. For instance, berberine and antimicrobial alkaloid isolated from *Berberis fremontii* has very weak antimicrobial activity in solution. However, in combination with other compound 5-Methoxy hydnocarpin (5-MHC) the antimicrobial activity of berberine is increased by 200 folds against *Staphylococcus aurues*[23]. Another interesting observation is the combination of piperine isolated from *Piper nigrum* with essential drugs, such as antibiotics, antihypertensive and antiepileptics as well as nutrients[24], phenytoin[25], pentobarbitone[26], theophylline[27] leading to 'dose economy' due to enhanced uptake, higher blood concentration and drug available for long duration in the body (U.S. Pat. No. 5,536,506; U.S. Pat. Nos. 5,616,593 and 5,972,382). Piperine has also been added in multi-drug formulations for the treatment of tuberculosis and leprosy. A formulation containing rifampicin, pyrazinamide and isoniazid has been tested in human volunteers (Indian Patent No. 1232/DEL/89). For most drugs, the comparative levels and peak concentration of the drugs in the presence of piperine were higher. We have recently demonstrated the bioenhancer activity of cow-urine distillate in a composition containing antibiotics and anticancer agents (U.S. Pat. No. 6,410,059). Thus, bioavailability enhancement helps to lower dosage levels and shorten the treatment course.

OBJECTS OF THE INVENTION

The main object of the present invention to identify a plant extract with bioactivity enhancement activity when used in combination with antibiotics, other drugs and nutrients.

Another object of the invention is to isolate, characterize and establish the nature of the biomolecule from the active plant extract with bioenhancer property.

Still another object of the invention is to test the bioavailability (absorption or uptake) enhancement of nutrients and drugs through gastro-intestinal membrane when used in conjunction with the bioenhancer.

Still another object of the invention is to identify the mechanism of action of the bioenhancer molecule using in vitro assays.

SUMMARY OF THE INVENTION

A new nitrile glycoside, niaziridin (1) has been isolated by bioactivity-guided fractionation from the pods of *Moringa oleifera*, which was able to increase the bioactivity of commonly used antibiotics such as rifampicin, tetracycline and ampicillin against Gram (+) and (−) bacteria. Further the molecule enhances the activity of antifungal drugs against *C.albicans* and increases the absorption of antibiotics and nutrients through gastro-intestinal membrane. Therefore, niaziridin can be used in combination therapy with antibiotics resulting in reduced drug associated toxicity, reduced cost and duration of chemotherapy.

Accordingly the present invention provides a novel nitrile glycoside of the formula I below and pharmaceutically acceptable derivatives and analogues thereof.

Formula I

In one embodiment of the invention, the derivative comprises a compound of formula II wherein when R is —C≡NN, $R_1$ is selected from the group consisting of $CH_3$, $CH_2CH_3$, $COCH_3$, $COCH_2CH_3$, benzoate, 3-nitrobenzoate, 4-nitrobenzoate, 3,4,5-trimethoxybenzoate, o-anisoate, m-anisoate, p-aniosate, laurate, 3,3-dimethylacrylate, crotonate, myristate, palmitate, pentoses hexoses and H, provided that when $R_1$ is selected from pentoses and hexoses, $R_2$ is also pentoses and hexoses respectively and when $R_1$ is H, $R_2$ is either pentoses or hexoses and R2 in all other cases is a compound of formula III

Formula II

Formula III

In another embodiment of the invention, in formula II when R is —N═C═S, $R_1$ is selected from the group consisting of $CH_3$, $CH_2CH_3$, $COCH_3$, $COCH_2CH_3$, benzoate, 3-nitrobenzoate, 4-nitrobenzoate, 3,4,5-trimethoxybenzoate, o-anisoate, m-anisoate, p-anisoate, laurate, 3,3-dimethylacrylate, crotonate, myristate, palmitate, pentoses hexoses and H, provided that when $R_1$ is a pentose, $R_2$ can be either pentose or hexose, and when $R_1$ is a hexose, $R_2$ is a hexose, and when $R_1$ is H, $R_2$ is either pentoses or hexoses and $R_2$ in all other cases is a compound of formula III.

The present invention also relates to a pharmaceutical composition comprising of a biologically active molecule and compound of formula I in an amount effective to enhance the biological activity and the bioavailability absorption through the gastro-intestinal membrane) of the drug molecule.

In one embodiment of the invention, the biologically active molecule is selected from a drug and nutraceutical.

In a further embodiment of the invention, the drug is selected from the group consisting of an antibiotic, antibacterial and anti-TB agent which is used in the treatment of both Gram (−) and Gram (+) bacterial infections including *Myobacterium tuberculosis*.

In another embodiment of the invention, the antibiotic is selected from the group consisting of aminoglycoside, rifampicin, penicillin, fluoroquinolone, and their clinically used derivatives.

In a further embodiment of the invention, the drug comprises an anti-tuberculosis agent selected from the group consisting of rifampicin, isoniazid, ethambutol, pyrazinamide and streptomycin.

In yet another embodiment of the invention, the drug comprises an antifungal agent used in the treatment of fungal infections.

In a further embodiment of the invention, the antifungal agent is an azole selected from the group consisting of azole, comprising of clotrimazole, micanozole, ketaconozole, flucanoazole and itracanozole.

In yet another embodiment of the invention, the antifungal agent comprises an antifungal agent effective against mycelial and yeast forms of fungi.

In yet another embodiment of the invention, the compound of formula I is present in a concentration between 0.1 µg/ml to 100 µg/ml.

In yet another embodiment of the invention, the compound of formula I is used in the form of a crude plant extract or enriched fraction isolated from the fruit pods of *Moringa oleifera*.

In yet another embodiment of the invention, the bioactivity of the biologically active molecule is enhanced to a range of 1.5 to 80 folds when used in combination with the compound of formula I.

In another embodiment of the invention, the nutraceutical is selected from the group consisting of vitamins, aminoacids, ions and nitrogenous bases.

The present invention also provides a process for the isolation of compound of formula I from *Moringa oleifera* comprising drying and grinding the seeds thereof, treating the dried and ground seeds with ethanol to obtain an ethanolic extract, subjecting the ethanolic extract to filtration, concentration and lyophilization to obtain a crude ethanolic extract of compound of formula I.

Formula I

In one embodiment of the invention, the seeds are air-dried at a temperature in the range of 30° C. to 45° C. and in shade.

In another embodiment of the invention, the dried and ground seeds were treated with ethanol at a temperature in the range of 30° C.–45° C. for a period of about 48 hours.

In another embodiment of the invention, the ethanol extract was concentrated at a temperature of about 40° C. and under reduced pressure.

In yet anther embodiment of the invention, the crude ethanolic extract was subjected to solvent fractionation to isolate the compound of formula I.

In another embodiment of the invention, the solvent partitioning was carried out by dissolving the crude ethanolic extract of compound of formula I in water, filtering the solution to obtain an insoluble portion and a portion soluble in water, dissolving the insoluble portion so obtained in methanol, extracting the soluble portion with Hexane followed by chloroform, ethyl acetate and n-butanol saturated with $H_2O$ respectively, concentrating all solvent portions obtained under reduced pressure.

In another embodiment of the invention, $NaSO_4$ (anhydrous) was added to each solvent fraction for removing moisture.

In yet another embodiment of the invention, all the solvent fractions were concentrated at 40° C. under reduced pressure.

DETAILED DESCRIPTION OF THE INVENTION

In our efforts to discover new biomolecules from plant sources which could function as bioactivity enhancer of commonly used but toxic antibiotics, nutraceuticals etc. we found that the ethanolic extract of the fruit pods with seeds of Moringa (*Moringa oleifera*) was able to enhance the activity of rifampicin, ampicillin and tetracycline against Gram (+) and Gram (−) bacteria including *Mycobacterium tuberculosis* the causal organism of tuberculosis. The active ethanolic extracts of the pods were then subjected to bioactivity-guided fractionation to yield a pure compound, which on chemical characterization was found to be niaziridin of the formula I. The compound I was able to increase the activity of antibiotics such as rifampicin, ampicillin and tetracycline against *Escherichia coli* (Kumar et al 1976; *J.Bacteriology* 125: 545), *Bacillus subtilis* (equivalent of ATCC 6015), *Mycobacterium smegmatis* (equivalent of ATCC 10231) and *M.tuberculasis* H37Rv. The compound was also able to enhance the activity of antifungal azole drugs such as clotrimazole against *C.albicans*, the causal organism of candidiasis. The compound was also able to facilitate the uptake of nutrients like Vitamine B12 through the intestinal gut membrane in combination, thus also functioning as bioavailability facilitator.

*M.oleifera* Lam. is a small and medium size tree, about 10 mt. height, belongs to the family Moringaceae and it is also known as 'Drumstick'. It is indigenous in the sub-Himalayan tract and cultivated throughout India and Burma. The tree is indigenous to North West India and is plentiful on recent alluvial land in or near sandy beds of rivers and streams. It is often cultivated in hedges and homeyards. It grows in all types of soils extract stiff clays and thrives best under the tropical peninsular climate of south India. The tree is valuated mainly for the tender pods, which are esteemed as vegetable. They are cut into slices and used in culinary preparations; they are also pickled. Flowers and tender leaves are eaten as potherb. Seeds are consumed after frying and are reported to taste like peanuts.

All parts of the tree are considered medicinal and used traditionally in the treatment of ascites, rheumatism, venomous bites and as cardiac and circulatory stimulants. Practitioners of Ayurveda prescribe roots of *M. oleifera* as stimulant, in treatment of intermittent fever, epilepsy and chronic rheumatism[1]. Roots are also useful as carminative, anthelmintic and diuretic. Bark is used as abortifacient, cardiac stimulant and antifungal. Leaves are utilized in inflammation, helmintheses and scurvy. Seeds are useful as purgative, antipyretic and anti-inflammatory[20].

Flowers are used as diuretic and cholagogue[21]. The leaves are rich in vitamins A and C and are considered useful in scurvy and catarrhal affection; they are also used as emetic. A paste of the leaves is used as an external application for wounds. Flowers are used as tonic, diuretic and cholagogue.

The seeds are considered antipyretic, acrid and bitter. The seed oil is applied in rheumatism and gout. Number of biomolecules has been isolated from different parts of moringa tree, which are detailed in Table 1.

TABLE 1

Chemical constiuents present in different parts of *M. oleifera*.

| Plant parts | Extract | Chemical constituents reported |
|---|---|---|
| Seeds | Benzene | Monopalmitic & trioleic triglycerides[2] oleic acid. |
|  | Hot water | 4[-a-L-rhamnosyloxy], Benzylisothiocyanate and 4-[a-L-rhamnosyloxy]phenylacetonitrile β-carotene, ascorbic acid[3]. |
| Pods | Ethanolic | Niazidin[4] |
| Flower | Aqueous | Thiamine, riboflavine, nicotinic acid, β carotene, ascorbic acid, D-glucose[5] |
| Leaves | Ethanolic | Thiocarbamate like niazinin A and niazinin B, niazimicin a mixture of niaziminins A and B, niazirin, niazirmin and a mustard oil glycoside 4-[(4'-O-acetyl-alpha-L-rhamnosyloxy)benzyl]-isothiocyanate[6,7,8] |
| Stem | Ethanolic | 4-thydroxymellein, vanillin, hydroxyproline[9]. |
| Roots | Ethanolic | Pterygospermin[10,11,12] |

The following biological activity is reported for the extracts and or compounds that have been isolated from the *M.oleifera* plant parts.

a) Anticancer Activity: Paste of *M. oleifera* leaves has been screened for its influence on the carcinogen detoxifying glutathione-s-transferasein swiss mice[13].

b) Antifertility activity: The aqueous extract of root and bark of *M. oleifera* at a dose of 200 mg/kg respectively showed post coital antifertility effect in rat and also induced foetal resorption at late pregnancy[14].

c) Anti-inflammatory Activity: Crude ethanolic extract of dried seeds was tested for anti-inflammatory activity using carrageenan induced inflammation in hind paw of mice[14,15].

d) Anti-ulcer Activity: The methanolic extract of leaves of *M oleifera* inhibited gastric lesion formation induced by aspirin serotonin or indomethacin in rats[16].

e) Cardiovascular Activity: Compounds niazinin A and B, niazimicin, niaziminin A and B isolated from the ethanolic extract of the leaves produced hypotensive and bradycardiac effect in anaesthetized rat at a dose of 1–10 mg/kg I.V[17].

f) Antimicrobial Activity: The antimicrobial activity of leaves, root, bark and seeds were investigated against bacteria, yeast, dermatophytes and helminths pathogenic to man. The fresh leaf juice and aqueous extract of seeds inhibited the growth of *Pseudomonas aeruginosa, Staphylococcus aureus*[18]. The extract of *M. oleifera* seeds at 1–10 dilution inhibited the growth of fungi like *Trichophyton rubrum* and *T. mentagrophytes*[19].

However, bioenhancement of antibiotics, antifungal drugs and nutrients by molecules from Moringa pods has not been reported anywhere.

The present invention provides a pharmaceutical composition comprising an effective amount of niaziridin as a bioactivity and bioavailability facilitator and pharmaceutically acceptable additives selected from antibiotics, drugs, therapeutic and nutraceutic agents and similar molecules which are targeted to the living systems.

Niaziridin can be used in antifungal therapy for the treatment fungal infection caused by yeasts such as *C.albicans*. The niaziridin can also be used in tuberculosis therapy in combination with rifampicin, isoniazid and other antitubercular agents.

Niaziridin the bioavailability facilitator helps in transferring the compounds, drugs and nutrients across the membrane and for better effectiveness on the target site.

The antibiotics are rifampicin, tetracycline, ampicillin, quinolones, fluoroquinolones, isoniazid and similar compounds; nutrients are vitamines, aminoacids, nitrogen bases; antifungal agents are azoles such as clotrimazole, ketaconazole, micanozole and itracanozole.

The compound of formula I functions as a bioavailability facilitator and helps the antibiotics and other molecules to act better on the target by increasing the effectiveness.

The living system may be bacteria, fungi or any living cells. Preferably Niaziridin is used in the range between 0.1 µg/ml to 10 µg/ml. In one feature, the lyophilized active fraction isolated from the pods of *Moringa oleifera* used is in the range between 0.1 µg/ml to 100 µg/ml. The bioactive fraction enhances the activity of anti-bacterial, anti-fungal and anti-tuberculosis agents from 2 to 80 folds.

The methodology followed by us for this screening included specifically designed bioassays described below as examples. The bacterial and fungal strains used in this invention were acquired commercially from Microbial Type Culture Collection (MTCC) at Institute of Microbial Technology (IMTECH), Chandigarh, India that possessed corresponding properties of the ATCC strain mentioned.

EXAMPLES

1. Collection and Extraction of Pod Materials:

20.0 kg of the *Moringa oleifera* pods were collected from local area of Lucknow. Pods were separated and air dried at room temperature (35° C.–40° C.) in shade. After air drying they were ground and sieved to fine powder in a mixer grind. 8 kg of the powdered pod materials were dipped in absolute ethanol in a percolator for 48 hrs at room temperature (35° C.–40° C.). Ethanol extract was filtered using Whatman filter paper No.1 and concentrated at the 40° C. under reduced pressure. The ethanolic extract was then lyophilized to obtain 208 g of crude extract. Stock of 100 mg/ml was made in DMSO and tested for bio enhancing activity. The results in table-2 indicate that the crude ethanolic extract prepared from the pods of *Moringa oleifera* was able to enhance the activity of rifampicin by 2.5 to 3.0 folds against *E.coli* CA 8000 (Kumar et al 1976; *J.Bacteriology* 125: 545).

TABLE 2

Bioenhacing activity of crude ethanolic extract of moringa pods @ 100 µg/ml in combination of rifampicin against *E. coli* (CA8000).

| Antibiotics (µg/ml) | Titre | % Survival | Fold Enhancement in activity of antibiotics as compared to rifampicin alone |
|---|---|---|---|
| Control (LB) | $1.4 \times 10^8$ | 100 | |
| Control (LB + crude extract) | $1.4 \times 10^8$ | 100 | |
| Rif (20) | $3.4 \times 10^7$ | 24.2 | — |
| Rif (20) + crude extract | $1.2 \times 10^7$ | 8.5 | 2.8 |
| Rif (30) | $3.0 \times 10^7$ | 21.4 | — |
| Rif (30) + crude extract | $1.2 \times 10^7$ | 8.5 | 2.5 |

2. Bioactivity Guided Fractionation:

Solvent fractionation of the active crude extracts was undertaken to isolate the active principle. 250 g ethanolic extract was dissolved in 500 ml of distilled water. Then it was filtered using Whatman No. 1 filter paper. The insoluble portion was dissolved in methanol and the soluble portion ($H_2O$) was extracted with Hexane, then chloroform, ethyl acetate and n-butanol (saturated with $H_2O$) respectively. $NaSO_4$ (anhydrous) was added to each fraction for removing the moisture.

All the solvent fractions were concentrated at 40° C. under reduced pressure and tested. The results indicate that ethyl acetate fraction obtained from the crude pod extract possessed the activity enhancement property.

TABLE 3

Enhancement of rifampicin activity by ethyl acetate fraction of active crude extract @ 10 µg/ml against *E. coli* (CA8000).

| Antibiotics (µg/ml) | Titre | % Survival | Fold Enhancement in the activity of antibiotics as compared to rifampicin alone |
|---|---|---|---|
| Control (LB) | $2.49 \times 10^8$ | | |
| Control (LB + EtOAc. Frac.) | $2.35 \times 10^8$ | | |
| Rif (20) | $1.00 \times 10^8$ | 40.0 | — |
| Rif (20) + EtOAc. Frac | $1.04 \times 10^7$ | 4.1 | 9.7 |
| Rif (30) | $5.81 \times 10^7$ | 23.3 | — |
| Rif (30) + EtOAc. Frac | $1.30 \times 10^7$ | 5.2 | 4.4 |

Column chromatography of the bioactive ethyl acetate fraction (7.0 g) was performed using silica gel. Different solvent systems were used for the elution of the column sub fractions starting with 100% hexane, then chloroform and then ethyl acetate. 150 ml of fraction were collected and ten such fractions were pooled for further bio-evaluation. The bioactivity enhancement of antibiotics was detected in fractions staring from 30% chloroform+70% ethyl acetate and upto 95% ethyl acetate+5% Methanol fractions. Thin layer chromatography (TLC) of the active column fractions was then performed by a procedure that is well documented and can be performed by a person skilled in the art of natural product isolation. All the spots developed by iodine treatment were separated, and redissolved in the appropriate solvent (methanol, ethyl acetate and chloroform) for bio-evaluation. The active spot was further purified five times by the same procedure to obtain 20 mg of single active TLC spot.

3. Characterization of the Active Pure Compound:

The active spot obtained by TLC was further purified by repetitive column chromatography which can be performed by a person skilled in the art and then analyzed by $^1H$ & $^{13}C$ NMR, LC-MS to determine the structure of the active pure compound. On the basis of spectroscopic data the new compound isolated from the pods of *Moringa oleifera* was characterized as niaziridin (formula I), a new nitrile glycoside from nature.

4. Bioactivity Enhancement of Antibiotics and Antifungal Agents in Combination:

Bioactivity enhancement of antibiotics was done by working out killing efficiency of antibiotics alone and in combination with bioenhancer (extract/pure compounds). Bacterial/yeast culture was grown in 6 ml nutrient broth and Sabouraud's dextrose broth respectively for 48 hours at 37° C. by inoculating a single colony. The culture was divided into 3 sections and fresh broth of 2.0 ml was added into each tube to made up to 4 ml. Test compounds @ 1.0 and 0.1 µg/ml were added into two of the culture tubes whereas methanol the solvent used for dissolving test compound was added in third tube to serve as a control. The cultures were grown at 37° C. for 4 hours in an incubator shaker at 200 rpm and centrifugal to pellet cells. Cells were washed once as above in sterile water or PBS. Pellet of each tube were then dissolved in 4 ml fresh broth and titre of cells were estimated from each tube by serial dilution and spread plating on NA. Colony counts obtained after incubation for 48 hours at 37° C. gave initial titre of cells in each tube. A series of tube containing 5 ml of NB with antibiotics of different concentration were prepared in three sets. 0.1 ml of culture pre-treated with test compounds (1.0 and 0.1 µg/ml) as well as from control tube was inoculated into series of tubes maintained in three sets. The tubes were incubated at 37° C. for 48 hours to obtain growth. 0.1 ml of culture was removed from all tubes and titre was estimated as before to give final titre. Results were calculated as fold enhancement in antibiotic killing action from initial and final titre of cells. It was evident from Table-4 that pure compound Niaziridin enhanced activity of commonly used antibiotics such as rifampicin, tetracycline, nalidixic acid etc against *E.coli* a Gram (−) bacteria. Therefore the compound was further tested for its bioenhancing property against representative Gram (+) bacterial species *Myobacterium smegmatis* and *B.subtilis*. Results in table-5 indicates that the compound enhanced activity of rifampicin, ampicillin, nalidixic acid by 1.2–19 folds against both the Gram (+) strains.

TABLE 4

Enhancement of antibiotic activity by Niaziridin (1) @ 0.1 µg/ml in combination with antibiotics against *E. coli* (CA8000).

| Antibiotics (µg/ml) | Titre | % Survival | Fold enhancement in killing over antibiotic alone. |
|---|---|---|---|
| Control (LB) | $1.1 \times 10^8$ | 100 | |
| Rif (20) | $1.5 \times 10^4$ | 0.0136 | — |
| Rif (20) + comp (1) * | $3.9 \times 10^3$ | 0.0035 | 38.8 |
| Rif (30) | $3.8 \times 10^4$ | 0.038 | — |
| Rif (30) + comp (1) | $3.0 \times 10^3$ | 0.003 | 12.6 |
| Control (LB) | $2.3 \times 10^8$ | 100 | |
| Amp (6) | $8.5 \times 10^6$ | 3.69 | — |
| Amp (6) + comp (1) | $1.6 \times 10^6$ | 0.69 | 5.3 |
| Control (LB) | $6.0 \times 10^8$ | 100 | |
| Tet (1) | $7.0 \times 10^6$ | 1.16 | — |
| Tet (1) + comp (1) | $3.0 \times 10^6$ | 0.5 | 2.3 |
| Tet (2) | $3.5 \times 10^6$ | 0.58 | — |
| Tet (2) + comp (1) | $7.5 \times 10^5$ | 0.11 | 5.2 |
| Control (LB) | $6.0 \times 10^8$ | 100 | |
| Nal (6) | $6.0 \times 10^6$ | 1.0 | — |
| Nal (6) + comp (1) | $1.2 \times 10^5$ | 0.02 | 50.0 |

* Compound refers to Niaziridin.

TABLE 5

Enhancement of antibiotic activity of Niaziridin (1) @ 1.0 µg/ml in combination with different antibiotics against Gram (+) bacteria *B. subtilis* and *M. smegmatis*.

| | *B. subtilis* (MTCC121) | | | *M. smegmatis* (MC² 155) | | |
|---|---|---|---|---|---|---|
| Treatment | Titre | % Survival | Folds enhancement in killing | Treatment | Titre | % Survival | Folds enhancement in killing |
| Control (LB) | $4.0 \times 10^8$ | 100.0 | | Control (LB) | $4.0 \times 10^7$ | 100.0 | |
| Rif (0.05) | $2.1 \times 10^8$ | 52.5 | | Rif (0.05) | $1.3 \times 10^7$ | 32.5 | |
| Rif (0.05) + comp (1) | $1.1 \times 10^7$ | 2.7 | 19.4 | Rif (0.05) + comp (1) | $6.7 \times 10^6$ | 16.75 | 1.9 |
| Control (LB) | $4.0 \times 10^8$ | 100.0 | | Control (LB) | $4.0 \times 10^8$ | 100.0 | |
| Amp (0.01) | $2.9 \times 10^8$ | 72.5 | | Amp (0.1) | $1.0 \times 10^8$ | 25.0 | |
| Amp (0.01) + comp (1) | $5.7 \times 10^7$ | 14.2 | 5.1 | Amp (0.1) + comp (1) | $2.1 \times 10^7$ | 5.25 | 4.7 |
| Control (LB) | $4.0 \times 10^8$ | 100.0 | | Control (LB) | $4.0 \times 10^8$ | 100.0 | |
| Tet (1.0) | $7.0 \times 10^7$ | 17.5 | | Tet (2.0) | $1.2 \times 10^8$ | 30.0 | |
| Tet (1.0) + | $2.0 \times 10^7$ | 5.0 | 3.5 | Tet (2.0) + | $3.0 \times 10^7$ | 7.5 | |

TABLE 5-continued

Enhancement of antibiotic activity of Niaziridin (1) @ 1.0 μg/ml in combination with different antibiotics against Gram (+) bacteria B. subtilis and M. smegmatis.

| | B. subtilis (MTCC121) | | | | M. smegmatis (MC² 155) | | |
|---|---|---|---|---|---|---|---|
| Treatment | Titre | % Survival | Folds enhancement in killing | Treatment | Titre | % Survival | Folds enhancement in killing |
| comp (1) | | | | comp (1) | | | 4.0 |
| Control (LB) | $4.0 \times 10^8$ | 100.0 | | Control (LB) | $4.0 \times 10^8$ | 100.0 | |
| Nal (2.0) | $3.1 \times 10^7$ | 7.75 | | Nal (1.0) | $3.7 \times 10^8$ | 92.5 | |
| Nal (2.0) + comp (1) | $4.6 \times 10^6$ | 1.1 | 7.0 | Nal (1.0) + comp (1) | $3.0 \times 10^8$ | 75.0 | 1.2 |

Further to determine whether the pure compound isolated from the pods of Moringa is able to enhance the activity of antifungal drugs, similar broth assays were done with clotrimazole, a commonly used azole group of antifungal agent against *Candida albicans*. The results indicate that (Table-6) the compound Niaziridin was able to enhance the antifungal activity of clotrimazole by 5–6 folds against *C.albicans* when present in combination. However, the antifungal activity enhancement was observed only at a relatively higher concentration (10 ug/ml) of the compound.

TABLE 6

Enhancement of anticandidial activity of clotrimazole (0.5 ug/ml) against *C. albicans* in combination with Niaziridin (10 ug/ml).

| | Cfu/ml at 36 h | | |
|---|---|---|---|
| Titre at 36 h in untreated control | Clotrimazole alone | Clotrimazole + Niaziridin | Fold enhancement of lethal activity |
| $1.6 \times 10^8$ | $23.6 \times 10^5$ | $4.5 \times 10^5$ | 5.2 |

5. Bioactivity Enhancement of Anti-Tubaercular Drugs Against *M.Tuberculosis* on BACTEC 460 TB System Since, the bioenhancer compound was able to enhance the activity of antibiotics against Gram (+) bacteria such as *M.smegmatis*, our subsequent interest was to test the compound against *M.tuberculosis* H37Rv (ATCC 27294) (Philipp et al 1996; *Proc.Nat.Acad.Sci. USA* 93, 3132–3137), the causal organism of tuberculosis. To accomplish this we employed a radiometric assay using the BACTEC 460 TB system manufactured by M/S Becton Dickinson Ltd., USA. The antimycobacterial property of the drugs in combination with the bioenhancer was studied as per the recommended drug sensitivity protocol prescribed by the manufacturer (BACTEC 460 TB system: Product & Procedure Manual, MA 0029, 1996; Becton Dickinson Co., USA). Briefly the procedure is described below.

(a) The 12 B vials as provided by the manufacture were pre-tested prior to inoculation to establish the recommended $CO_2$ atmosphere. The vials that showed a growth index (GI) of 20 or more on the initial test were ejected.
(b) 100 μl of the mycobacterial suspension indicating a GI value of 500 were inoculated into 12B containing the antibiotics.
(c) In the control vial 1:100 fold diluted inoculum was used by transferring 0.1 ml of the suspension into 9.9 ml of special diluting fluid. After mixing thoroughly, 0.1 ml of this dilution was added into the control 12 B vial (without a drug).
(d) Biosafety precautions were taken as recommended by the manufacturer.
(e) Vials were tested daily in BACTEC 460 TB system for 12 days at approximately the same time each day as recommended by the manufacturer. The mycobacterial growth is expressed by Growth Index (GI) and compared to that of the control vials (antibiotic alone).

Figure 1:
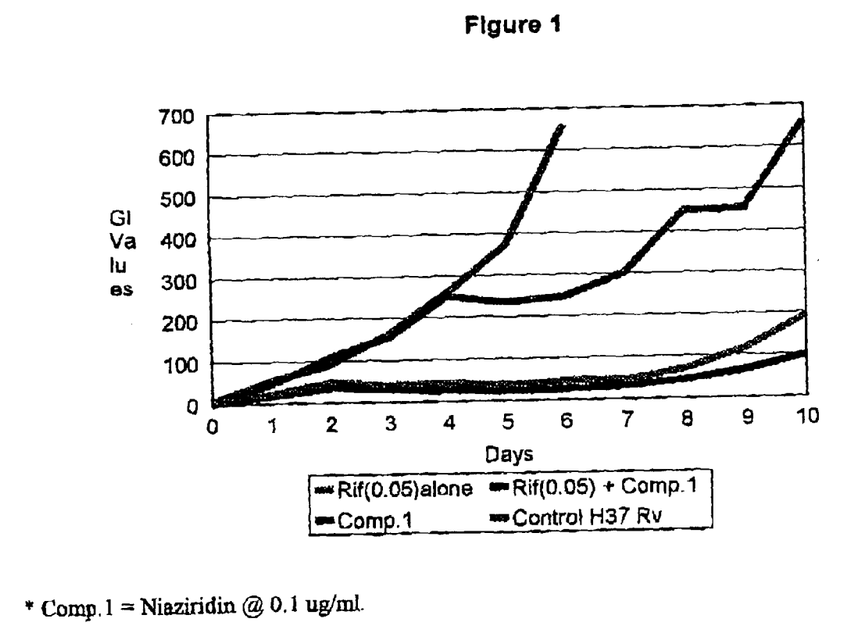
FIG. 1 is a potentiation graph of rifampicin activity against *Myobacterium tuberculosis* (H37Rv) by the compound of the invention.
Figure 2:
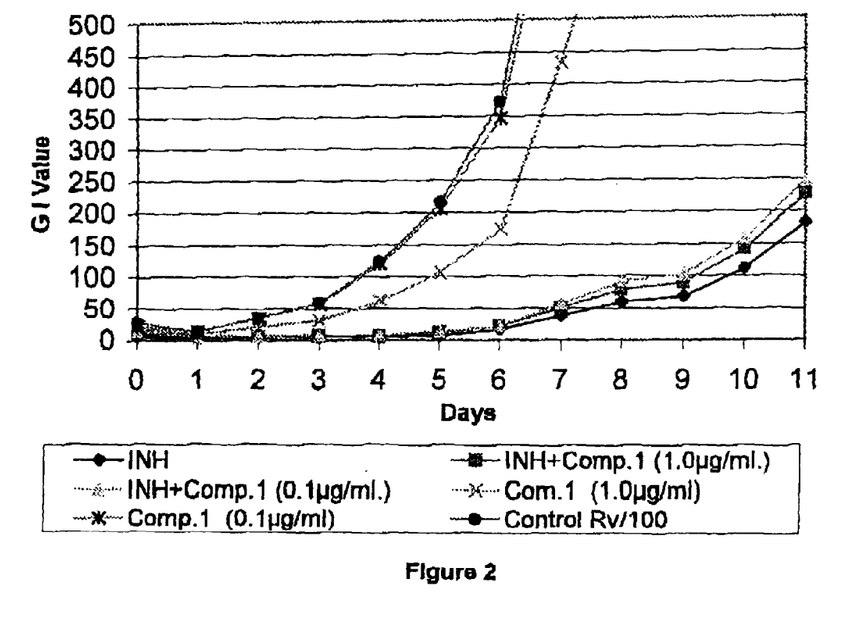
FIG. 2 is a potentiation graph of isoniazid activity against *Myobacterium tuberculosis* (H37Rv) by the compound of the invention.
Figure 3:
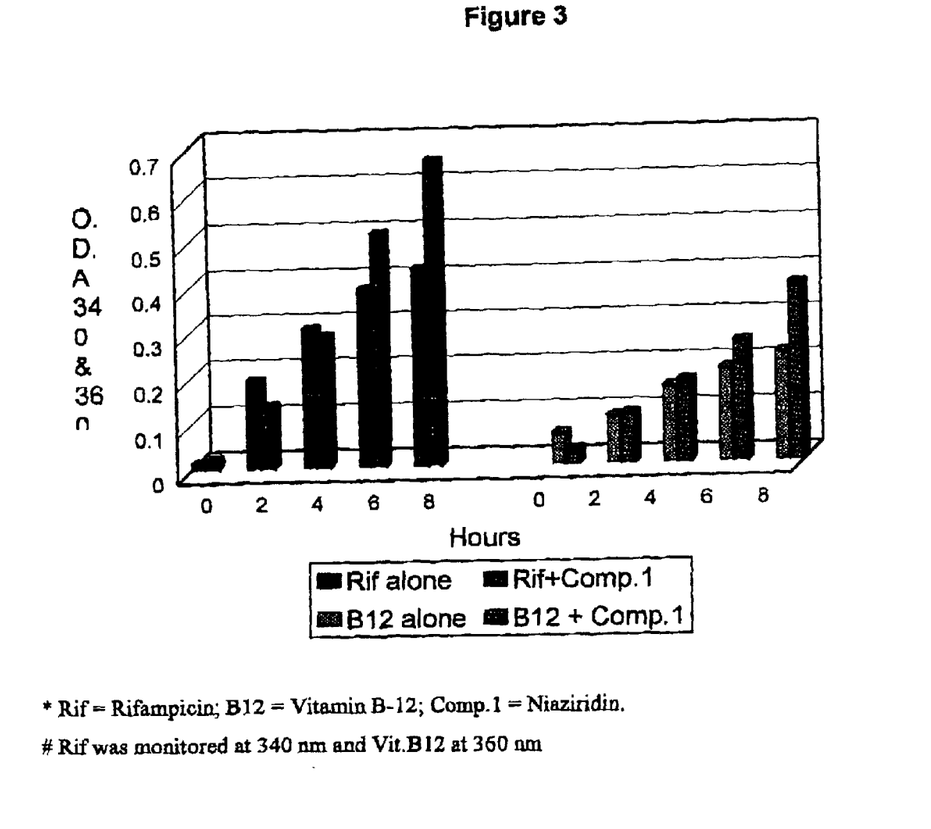
FIG. 3 is a graph of the in vitro availability of rifampicin and vitamin B12 through the gastrointestinal tract in the presence of the compound of the invention.

It is evident from FIGS. 1 and 2 that the compound Niaziridin was able to enhance the antimycobacterial activity of rifampicin and isoniazid against the virulent strains of *M.tuberculsis*.

6. Bio Availability Test Using Gastro-Intestinal Epithelium

Specially designed U-tubes of glass consisting of two components (opposite-L type) were used in which one open end of an L-shaped was tapered to fit within the end of the other L-tube (as described in U.S. Pat. No. 6,410,059). The membrane of goat gut (initial part) was stretched and fixed to act as the barrier between the two ends such that by joining the two L-tubes, a U-tube was made. Sterile distilled water was then filled in both the sides to equal height/level. The antibiotic/compound was added to the donor tube (tapered) and through spectro-photometer, the transfer of molecule was observed using UV and visible absorption maxima of the respective molecules by taking the OD at defined wavelengths (264 nm for isoniazid).

7. Enhancement of Adsorption of λ☐ Phage on Bacteria

Overnight grown bacterial culture (*Escherichia coli*, CA 8000) was divided into 5 ml of aliquot each in screw cap tubes. One of the tube with the bacterial culture was treated with niaziridin to a final concentration of 1 μg/ml. Both the control and the treated tubes were incubated at 37° C. for 4 hours. The cultures were then infected with λ phage (MOI= 10) for 10 minutes at 37° C. (for adsorption) followed by centrifugation at 10000 RPM for 10 minutes at 4° C.

The supernatant and the pellets for both treated and untreated cultures were then compared for the phage titer by plating on top agar containing sensitive bacteria at different dilutions. The phage titer in the supernatant of the treated culture was reduced by 2.6 folds indicating increase in adsorption to the bacterial cells harvested in the pellet.

TABLE 7

Effect of plant compound, niaziridin on λ phage adsorption on *E. coli* cells.

| | Untreated cells | | Cells pretreated with niaziridin @ 1 ug/ml | |
|---|---|---|---|---|
| Multiplicity of infection (MOI) | Supernatant ($10^7$ pfu) | Pellet ($10^7$ pfu) | Supernatant ($10^7$ pfu) | Pellet ($10^7$ pfu) |
| 10 | 21.4 | 19.0 | 8.0 | 18.0 |
| 5 | 11.0 | 0.5 | 7.7 | 7.7 |

8. Enhancement of Bacterial Transformation

Overnight grown bacterial *E. coli* DH5α (Sambrook at al[28]) cells were diluted to 10 folds in growth medium and treated with niaziridin @1–10 μg/ml for 4 hours at 37° C. in a shaker (200 RPM).

These log phase cells were then treated with calcium chloride to induce competence and then transformed with pUC18 plasmid DNA and plated on Luria agar plates containing 100 μg/ml ampicillin. The detailed procedure can be found in Sambrook at al[28].

The colonies thus appeared, on the plates for both treated and untreated cultures were scored. An increase of 2.3 folds for transformation was observed in case of the strain DH5α□ and 5.5 folds in case of CA8000 indicating that the compound enhances the uptake of plasmid DNA in *E. coli* cells.

| | *E. coli* strains | | | |
|---|---|---|---|---|
| | CA8000 | | DH5α | |
| Cells pretreated with niaziridin at | Titre ($10^3$) | Fold enhancement in DNA transformation | Titre ($10^4$) | Fold enhancement in DNA transformation |
| 10 ug/ml | 24.0 | 5.5 | 20.0 | 2.3 |
| 1 ug/ml | 8.30 | 1.9 | 16.0 | 1.9 |
| Untreated Control | 4.3 | — | 8.4 | — |

References

1. Kirtikar K R, Basu B D. *Indian Medicinal Plants*. (M/S Bishen Singh, Mahendra Pal Singh, New Cannaught Place, Dehra Dun), 1975, Vol 1, Ed.2, 675–683.
2. Memon G M, Khatri L M, *Pak J Sci Ind Res*, 1987, 30 (5), 393–395.
3. Dayrit F M, Alcantar A D, Villasenor I M. *Philipp J Sci*, 1990, 119 (1), 23–32.
4. Faizi S et al. *J. Nat. prod.* 1997, 60 (12), 1317–1321.
5. Dahot M U. *Pak J Biochem*, 1988, 21 (1–2), 21–24).
6. Faizi S, Siddiqui B S. *Phytochemistry*, 1995,38 (4), 957–963.
7. Faizi S, et al. *J. Chem. Soc Perkin, Trans*, 1994,1 (20),3035–3040.
8. Faizi S, et al. *J. Nat prod*, 1994, 57 (9),1256–1261.
9. Saluja M J P, Kapkil R S, Popli S P. *Ind. J Chem*, 1978, Vol. 16 B (11), 1044–1055.
10. Narsimharao P L, Kurup P A. *J. Ind Inst Sci*, 1952, 34 (3) 219–227.
11. Raghunandanrao R, George M. *Ind J Med Res*, 1949, 37, 159–167.
12. Raghunandanrao R George M. *Nature*, 1946, 158, 745.
13. Aruna K, Sivaramakrishnan V M. *Ind J Exp Biol*, 1990,28 (11), 1008–1011.
14. Guevara A P, Vargas C, Milagros U Y. *Philipp J Sci*, 1996, 125 (3), 175–184.
15. Biswas A R, et al, *Med. Sci Res*, 1988 16 (23), 1219–1220.
16. Pal S K, et al. *Phytother Res*, 1995, 9 (6) 463–465.
17. Gilani A H, et al, *Phytother Res*, 1994, 8 (2), 87–91.
18. Caceres A, et al, *J. Ethnopharmacol*, 1991, 33 (3), 213–216.
19. Nwosu M O, Okafor J L. *Mycoses*, 1995,38 (5–6), 191–195.
20. Warrier P K, Nambiar V P K, Ramankutty C. *Compendium of India Medicinal Plants*, 1997, Vol.4.59.
21. Anonymous "*The Wealth of India Raw material*", CSIR, New Delhi, 1984, Vol.6 426–427.
22. Menon, 1983; Pulmonary Tuberculosis. *Bulletin of International Union against Tuberculosis*, India, 158–177.
23. Stermitz et al 2000, *Proc. Natl. Acad. Sci. (USA)* 97: 1433–1437.
24. Zutshi, U. et al. (1984) *Journal of the Association of Physicians of India*, 33, 223–224.
25. Bano et al., *Planta Medica*, 1987, pp. 568–569.
26. Majumdar, A. N. et al. (1990), *Indian Journal of Experimental Biology*, 28, 486–487.
27. Bano et al., *Eur. J. Clin. Pharmacol.* (1991) 41:615–617.
28. Sambrook et al. Molecular Cloning: A laboratory Manual (Third Edition), CSHL Press.

We claim:

1. A nitrile glycoside of the formula I:

Formula I

2. A pharmaceutical composition comprising a biologically active molecule and a compound of formula I in an amount effective to enhance the biological activity and the bioavailability absorption through a gastro-intestinal membrane of the molecule.

3. A composition as claimed in claim 2 wherein the biologically active molecule is selected from a drug and nutraceutical.

4. A composition as claimed in claim 3 wherein the drug is selected from the group consisting of an antibiotic, antibacterial and anti-TB agent which is useful in the treatment of both Gram (−) and Gram (+) bacterial infections including *Mycobacterium tuberculosis*.

5. A composition as claimed in claim 4 wherein the antibiotic is selected from the group consisting of aminoglycoside, rifampicin, penicillin, fluoroquinolone, and their clinically acceptable derivatives.

6. A composition as claimed in claim 3 wherein the drug comprises an anti-tuberculosis agent selected from the group consisting of rifampicin, isoniazid, ethambutol, pyrazinamide and streptomycin.

7. A composition as claimed in claim 3 wherein the drug comprises an antifungal agent useful in the treatment of fungal infections.

8. A composition as claimed in claim 7 wherein the antifungal agent is an azole selected from the group consisting of clotrimazole, micanozole, ketaconozole, flucanoazole and itracanozole.

9. A composition as claimed in claim 3 wherein the drug comprises an antifungal agent effective against mycelial and yeast forms of fungi.

10. A composition as claimed in claim 2 wherein the compound of formula I is present in a concentration of between 0.1 $\mu$/ml to 100 $\mu$g/ml.

11. A composition as claimed in claim 2 wherein the compound of formula I is in the form of a crude plant extract or enriched fraction isolated from the fruit pods of *Moringa oleifera*.

12. A composition as claimed in claim 2 wherein the biologically active molecule has a bio-activity that is enhanced to a range of 1.5 to 80 fold when used in combination with the compound of formula I.

13. A composition as claimed in claim 3 wherein the nutraceutical is selected from the group consisting of vitamins, aminoacids, ions and nitrogenous bases.

14. A process for the isolation of a compound of formula I from *Moringa oleifera* comprising drying and grinding seeds thereof, treating the dried and ground seeds with ethanol to obtain an ethanolic extract, subjecting the ethanolic extract to filtration, concentration and lyophilization to obtain a crude ethanolic extract of the compound of formula I Formula I 15. A process as claimed in claim 14 wherein the seeds are air-dried at a temperature in the range of 30° C. to 45° C. and in shade.

16. A process as claimed in claim 14 wherein the dried and ground seeds are treated with ethanol at temperature in the range of 30° C.–45° C. for a period of about 48 hours.

17. A process as claimed in claim 14 wherein the ethanol extract is concentrated at a temperature of about 40° C. and under reduced pressure.

18. A process as claimed in claim 14 wherein the crude ethanolic extract is subjected to solvent fractionation to isolate the compound of formula I.

19. A process as claimed in claim 18 wherein the solvent fractionation is carried out by dissolving the crude ethanolic extract of compound of formula I in water, filtering the solution to obtain an insoluble portion and a portion soluble in water, dissolving the insoluble portion so obtained in methanol, extracting the soluble portion with hexane followed by chloroform, ethyl acetate and n-butanol saturated with $H_2O$ respectively, and concentrating all solvent portions obtained under reduced pressure.

20. A process as claimed in claim 18 wherein anhydrous $NaSO_4$ is added to each solvent fraction for removing moisture.

21. A process as claimed in claim 18 wherein all the solvent fractions are concentrated at 40° C. under reduced pressure.

* * * * *